(12) United States Patent
Zhu et al.

(10) Patent No.: US 11,684,393 B2
(45) Date of Patent: Jun. 27, 2023

(54) ADJUSTABLE DOUBLE-SLOT INTERNAL SPINAL FIXATION APPARATUS AND BONE SCREW

(71) Applicant: SHANGHAI SANYOU MEDICAL CO.,LTD., Shanghai (CN)

(72) Inventors: Zezhang Zhu, Shanghai (CN); Yong Qiu, Shanghai (CN); Michael Mingyan Liu, Shanghai (CN); Ruifeng Liu, Shanghai (CN)

(73) Assignee: SHANGHAI SANYOU MEDICAL CO., LTD., Shanghai (CN)

( * ) Notice: Subject to any disclaimer, the term of this patent is extended or adjusted under 35 U.S.C. 154(b) by 0 days.

(21) Appl. No.: 16/482,712

(22) PCT Filed: Apr. 10, 2018

(86) PCT No.: PCT/CN2018/082550
§ 371 (c)(1),
(2) Date: Aug. 1, 2019

(87) PCT Pub. No.: WO2019/062070
PCT Pub. Date: Apr. 4, 2019

(65) Prior Publication Data
US 2020/0305933 A1 Oct. 1, 2020

(30) Foreign Application Priority Data

Sep. 27, 2017 (CN) .......................... 201710892210.X
Sep. 27, 2017 (CN) ........................... 201721255595.0

(51) Int. Cl.
A61B 17/70 (2006.01)

(52) U.S. Cl.
CPC ........ A61B 17/7032 (2013.01); A61B 17/704 (2013.01)

(58) Field of Classification Search
None
See application file for complete search history.

(56) References Cited

U.S. PATENT DOCUMENTS

| 216,338 A * | 6/1879 | Morgan ................ F16B 11/006 |
| | | 403/375 |
| 8,021,397 B2 * | 9/2011 | Farris ................. A61B 17/7041 |
| | | 606/269 |

(Continued)

FOREIGN PATENT DOCUMENTS

| CN | 101984925 A | 3/2011 |
| CN | 201930058 U | 8/2011 |

(Continued)

Primary Examiner — Julianna A Harvey

(57) ABSTRACT

The present disclosure provides an adjustable double-slot internal spinal fixation apparatus, including a first base, a second base and a connecting rod. The first base and the second base each contains a U-shaped slot from top to bottom. An inner wall of each U-shaped slot contains inner threads. The connecting rod is disposed along a horizontal direction. The second base contains a long slot along the horizontal direction. One end of the connecting rod is inserted in the first base, and the other end of the connecting rod is inserted in the long slot of the second base. The connecting rod can swing in the long slot. The first base and the second base are capable of relatively rotating on the connecting rod.

5 Claims, 9 Drawing Sheets

(56) References Cited

U.S. PATENT DOCUMENTS

| | | | |
|---|---|---|---|
| 2004/0204711 A1* | 10/2004 | Jackson | A61B 17/7035 606/308 |
| 2007/0233062 A1* | 10/2007 | Berry | A61B 17/7041 606/914 |
| 2009/0043339 A1 | 2/2009 | Tepper et al. | |
| 2011/0160778 A1* | 6/2011 | Elsbury | A61B 17/7037 606/305 |
| 2013/0006307 A1* | 1/2013 | Robinson | A61B 17/8695 606/252 |
| 2013/0331894 A1* | 12/2013 | Wei | A61B 17/7083 606/308 |
| 2015/0073488 A1* | 3/2015 | Rinner | A61B 17/7076 606/305 |
| 2017/0128107 A1 | 5/2017 | Alsup et al. | |
| 2017/0209184 A1* | 7/2017 | Fiechter | A61B 17/7032 |
| 2018/0280062 A1* | 10/2018 | Lee | A61B 17/705 |
| 2018/0280063 A1* | 10/2018 | Lee | A61B 17/7052 |
| 2018/0325569 A1* | 11/2018 | Ramsay | A61B 17/7037 |
| 2021/0177468 A1* | 6/2021 | Murray | A61B 17/7002 |

FOREIGN PATENT DOCUMENTS

| | | | | |
|---|---|---|---|---|
| CN | 102488548 A | 6/2012 | | |
| CN | 102573679 A | 7/2012 | | |
| CN | 102596067 A | 7/2012 | | |
| CN | 205458984 U | 8/2016 | | |
| EP | 3184063 A1 * | 6/2017 | | A61B 17/7002 |

* cited by examiner

ADJUSTABLE DOUBLE-SLOT INTERNAL SPINAL FIXATION APPARATUS AND BONE SCREW

CROSS REFERENCE TO RELATED APPLICATION

This is a Sect. 371 National Stage of PCT International Application No. PCT/CN2018/082550, filed on Apr. 10, 2018, which claims priority of a Chinese Patent Application No. CN 201710892210X, entitled "Adjustable Double-Slot Internal Spinal Fixation Apparatus and Bone Screw", filed with CNIPA on Sep. 27, 2017, and claims priority of a Chinese Patent Application No. CN 2017212555950, entitled "Adjustable Double-Slot Internal Spinal Fixation Apparatus and Bone Screw", filed with CNIPA on Sep. 27, 2017, the contents of the applications hereby are incorporated by reference.

BACKGROUND OF THE PRESENT INVENTION

Field of Invention

The present disclosure relates to internal spinal fixation medical instruments, and in particular to an adjustable double-slot internal spinal fixation apparatus and a bone screw.

Description of Related Arts

The internal spinal fixation technique is a surgical technique widely used for spinal diseases at present. Early internal fixation surgeries are very simple, for example, a cervical vertebra fusion surgery which fixes cervical vertebra by using silver wires. Development of the internal spinal fixation technique is mainly intended to meet the requirement of spine orthopaedy, for example, anterior or posterior scoliosis correction, and multi-stage restoration for spinal deformity. The pedicle screw technique is a milestone in the development of the internal spinal fixation technique. The pedicle screw fixation technique has become the core of the internal spinal fixation technique at present.

Currently, common internal spinal fixation apparatus includes various pedicle screws used in combination with rods and other auxiliary instruments. At present, the pedicle screws include single-slot pedicle screw (single-slot screw for short) and double-slot pedicle screw (double-slot screw for short).

The single-slot screw is usually used in surgeries for spinal degenerative change, spondylolisthesis, tumor, fracture, and the like. The double-slot screw is suitable for osteotomy as well as compound fixation and revision surgeries for lumbosacral and hip bones. When the osteotomy is needed, the double-slot screws can ensure a stable operation space for the osteotomy, effectively lower the risk of spinal cord injury, and achieve an orthopedic effect. During compound fixation, a rod in one of the slots is used for sacral bone fixation, and a rod in the other slot is used for hip bone fixation.

The foregoing double-slot screws can make surgeries more convenient, but still have some problems. For example, when mounted on a double-slot screw, two rods need to be fixed parallel, which will increase the number of fracturing and bending the rods. It is well known in the field that in order to achieve a correction effect, the rods are highly rigid. Different patients have different actual conditions, it is time-consuming to bend a rod at the time of surgery, and it is likely that the rod still fails to meet the requirements after being bent repeatedly. This will cause a concentrated stress of the rod or scratches on the rod. As a result, the service life is severely affected, and the rod fails easily.

SUMMARY OF THE PRESENT INVENTION

Double-slot screws can make surgeries more convenient, but still have some problems. For example, when mounted on a double-slot screw, two rods need to be fixed parallel, which will increase the number of fracturing and bending the rods. It is well known in the field that in order to achieve a correction effect, the rods are highly rigid. Different patients have different actual conditions, it is time-consuming to bend a rod at the time of surgery, and it is likely that the rod still fails to meet the requirements after being bent repeatedly. This will cause a concentrated stress of the rod or scratches on the rod. As a result, the service life is severely affected, and the rod fails easily.

A technical problem to be resolved by the present application is to provide an adjustable double-slot internal spinal fixation apparatus that reduces the number of rod bending and ensure the service life of rods, to overcome the defects in the prior art.

The present application uses the following technical solutions: an adjustable double-slot internal spinal fixation apparatus, comprising a first base, a second base and a connecting rod. The first base and the second base each contains a U-shaped slot from top to bottom. An inner wall of each U-shaped slot contains inner threads. The connecting rod is disposed along a horizontal direction. The second base contains a long slot along the horizontal direction. One end of the connecting rod is inserted in the first base and the other end of the connecting rod is inserted in the long slot of the second base. The connecting rod is capable of swinging in the long slot. The first base and the second base are capable of relatively rotating on the connecting rod.

Preferably, one end of the connecting rod is fixedly inserted in the first base, and the other end of the connecting rod is inserted in the second base in a rotatable manner.

Further, the U-shaped slot on the second base is connected with the long slot. A pressing block is disposed in the U-shaped slot of the second base. A limit bump is included on a bottom surface of the pressing block. The connecting rod contains an annular groove. The connecting rod is inserted to the bottom of the U-shaped slot through the long slot, and the limit bump on the pressing block fits with the annular groove on the connecting rod.

Preferably, one end of the connecting rod is inserted in the first base in a rotatable manner, and the other end of the connecting rod is inserted in the second base in a rotatable manner.

Further, the U-shaped slot on the second base is connected with the long slot. The U-shaped slots of the first base and the second base each contains a pressing block having identical structures. Limit bumps are included on bottom surfaces of the pressing blocks. Two ends of the connecting rod contain annular grooves respectively. One end of the connecting rod is inserted to the bottom of the U-shaped slot of the first base and the other end of the connecting rod is inserted to the bottom of the U-shaped slot of the second base through the long slot. The limit bumps on the pressing blocks fit with the annular grooves on the connecting rod.

Preferably, two side walls of the U-shaped slot of the first base and/or two side walls of the U-shaped slot of the second base each contains a fracture notch.

The present application further provides a convenient and flexible bone screw having the internal fixation apparatus, and the specific technical solution is as follows: the first base 1 and/or the second base each contains a screw rod.

Preferably, the first base and/or the second base each contains a ball socket, one end of the screw rod contains a ball head, and the ball head fits with the ball socket.

Preferably, the first base and/or the second base each contains a threaded hole, and the screw rod fits with the threaded hole through threads.

As described above, the adjustable double-slot internal spinal fixation apparatus and the bone screw according to the present application have the following beneficial effects:

capable of relative rotation and relative swing, and adjust positions according to rods, to achieve transition and guiding effects, thereby reducing the number of rod bending times and also alleviating the stress concentration of the rods or scratches on the rods that are caused by rod bending. Therefore, the service life of the rods can be ensured, thereby preventing the rods from failing earlier than expected. In addition, because the number of rod bendings can be reduced in actual use, surgery efficiency can be effectively improved, thereby significantly facilitating surgical operations for doctors and effectively reducing the labor intensity and workload of the doctors The bone screw according to the present application having the internal fixation apparatus is convenient and flexible, and achieves a good working effect.

| | |
|---|---|
| 1 First base | 2 Second base |
| 3 Connecting rod | 4 U-shaped slot |
| 5 Pressing block | 31 Annular groove |
| 51 Limit bump | 21 Long slot |
| 52 Inner plate | 53 Outer plate |
| 54 Gap | 6 Screw rod |
| 7 Rod | 8 Pressure head |
| 61 Ball head | 11 Through hole |
| 10 Vertebra | 211 Large-opening portion |
| 212 Small-opening portion | 41 Fracture notch |

DETAILED DESCRIPTION OF THE PREFERRED EMBODIMENTS

The structures, scales, sizes and the like drawn in the accompanying drawings of this specification are all merely used to cooperate with the content disclosed in the specification to help those skilled in the art understand and read the content, but are not used to define limiting conditions for implementing the present disclosure and therefore do not have any substantial technical meanings. Any modifications on the structures, changes in the scale relations or adjustment in the sizes that do not affect the efficacy and objects of the present disclosure should still fall within the scope covered by the technical content disclosed by the present disclosure. Meanwhile, terms such as "upper", "lower", "front", "rear", and "middle" mentioned in this specification are merely used for the clarity of the description, and are not intended to limit the implementation scope of the present disclosure. Changes or adjustments in relative relations thereof without changing the technical content substantially should also be considered as the implementation scope of the present disclosure.

In a spinal surgery, it is inconvenient to implant bone screws at some positions, but rods are needed to realize position correction or transition. The present internal fixation apparatus is used at such positions and can facilitate the spinal surgery.

Figure 3:
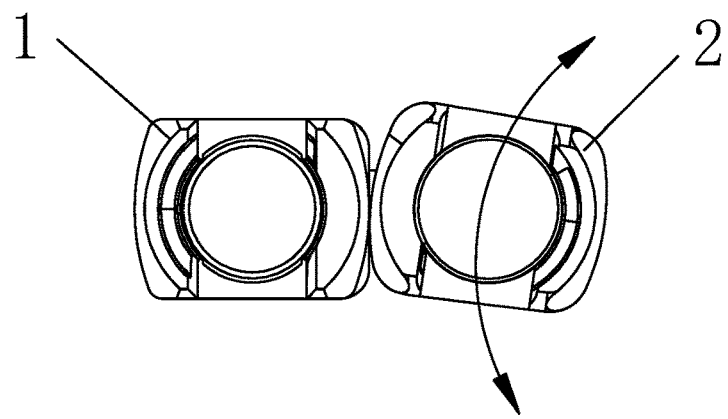
FIG. 3 is a top schematic diagram of swing of a first base and a second base in the present disclosure.

As shown in FIGS. 1-5, the present disclosure provides an adjustable double-slot internal spinal fixation apparatus, including a first base 1, a second base 2, and a connecting rod 3. The first base 1 and the second base 2 each contains a U-shaped slot 4 from top to bottom. An inner wall of each U-shaped slot 4 contains inner threads. The connecting rod 3 is disposed along a horizontal direction. The second base 2 contains a long slot 21 along the horizontal direction. One end of the connecting rod 3 is inserted in the first base 1, and the other end of the connecting rod 3 is inserted in the long slot 21 of the second base 2. The connecting rod 3 can swing in the long slot 21, that is, the first base 1 and the second base 2 swing relatively in the horizontal direction as shown in FIG. 3; the first base 1 and the second base 2 rotate relatively on the connecting rod 3.

The principle of the present disclosure is as follows: the first base 1 and the second base 2 are connected into an integrated structure through the connecting rod 3, during use, medical rods are disposed in the U-shaped slots 4 of the two bases respectively, and then tightly pressing the rods in the U-shaped slots 4 respectively by pressing caps in combination with the inner threads of the U-shaped slots 4. The two bases rotate and swing relatively, thereby driving the rods to adjust the positions flexibly. The rods will not be bent multiple times, which alleviates stress concentration and scratches, so that the rods are less likely to fail, and the service life ensured.

Figure 4:
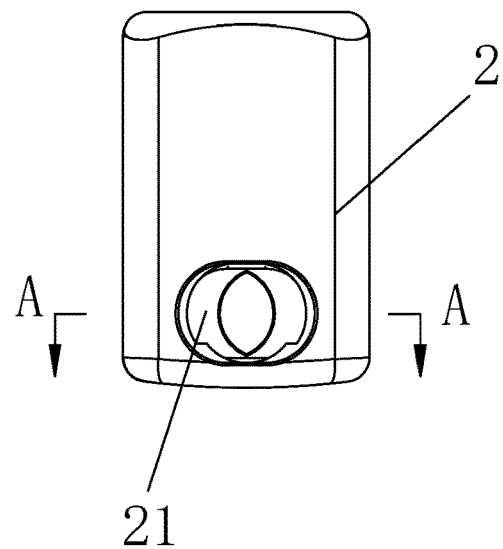
FIG. 4 is a front view of the second base in the present disclosure.
Figure 5:
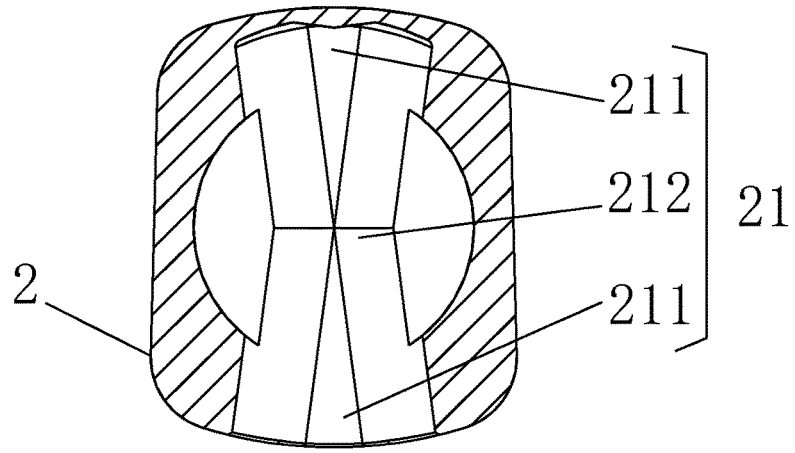
FIG. 5 is a cross-sectional view along A-A in FIG. 4.

With reference to FIGS. 2-5, the width of the long slot 21 on the first base 2 in the present disclosure is in the left-right direction in FIG. 4. The structure of the long slot 21 is shown in FIG. 5, where two end portions are large-opening portions 211 with large width, and the middle portion is a small-opening portion 212 with small width. The small-opening portion 212 in the middle can effectively limit the position of the connecting rod 3 during swing. In other words, the connecting rod 3 swings with the small-opening portion 212 in the middle as a center, to ensure the stability of the first base 1 and the second base 2 during swing.

Embodiment 1

Figure 6:
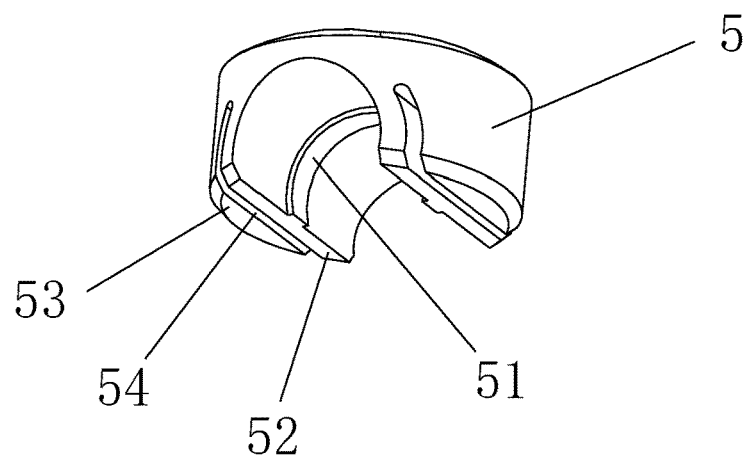
FIG. 6 is a structural diagram of a pressing block in the present disclosure.

A first structure of the adjustable double-slot internal spinal fixation apparatus according to the present disclosure is that one end of the connecting rod 3 is fixedly inserted in the first base 1, and the other end of the connecting rod 3 is inserted in the second base 2 in a rotatable manner, so that the two bases rotate relatively. Referring to FIG. 2 to FIG. 7, the U-shaped slot 4 is connected with the long slot 21. A pressing block 5 is disposed in the U-shaped slot 4 of the second base 2. A limit bump 51 is included on a bottom surface of the pressing block 5. The connecting rod 3 contains an annular groove 31. The connecting rod 3 is inserted to the bottom of the U-shaped slot 4 through the long slot 21. The limit bump 51 on the pressing block 5 matches the annular groove 31 on the connecting rod 3. That is, during use, when an end portion of the connecting rod 3 is inserted to the long slot 21 of the second base 2, the annular groove 31 of the connecting rod 3 can be seen through the U-shaped slot 4. When the pressing block 5 is put into the U-shaped slot 4, the limit bump 51 enters the annular groove 31 for limiting, so that the connecting rod 3 rotates with respect to the pressing block 5, in other words, the first base 2 rotates around the connecting rod 3 freely, thereby achieving relative rotation between the first base 1 and the second base 2. In this embodiment, the limit bump 51 and the annular groove 31 fitting with each other can limit the position of the second base 2 on the connecting rod 3. The distance between the first base 1 and the second base 2 is determined, that is, the distance between the two bases can be arranged according to the position of the annular groove 31 to obtain products of multiple models. In addition, relative swing between the connecting rod 3 and the second base 2 can be implemented in the following manners: (1) The pressing block 5 rotates in a horizontal plane independent of the second base 2, and the pressing block 5 rotates synchronously with the connecting rod 3 when the connecting rod 3 swings. (2) The pressing block 5 is made of an elastic material, when the connecting rod 3 rotates, the pressing block 5 is elastically deformed to facilitate swing of the connecting rod 3. In this embodiment, as shown in FIG. 6, the pressing block 5 has an inverted U-shaped structure adapted to the shape of the connecting rod 3, the inverted U-shaped structure contains an inner plate 52 and an outer plate 53 at each end. A gap 54 is included between the inner plate 52 and the outer plate 53. The inner plate 52 can be elastically deformed. The limit bump 51 is disposed on the inner plate 52. A side of the inner plate 52 facing the connecting rod 3 has a shape adapted to an outer wall of the connecting rod 3. When the pressing block 5 is pressed on the connecting rod 3, two inner plates 52 first expand outward and then retract, to be effectively attached to the connecting rod 3. The gap 54 provides a space for the expansion and retraction of the inner plates 52. When the connecting rod 3 swings with respect to the second base 2, the pressing block 5 is static with respect to the connecting rod 3, and rotates around the small-opening portion 212 as the connecting rod 3 swings.

Embodiment 2

Figure 7:
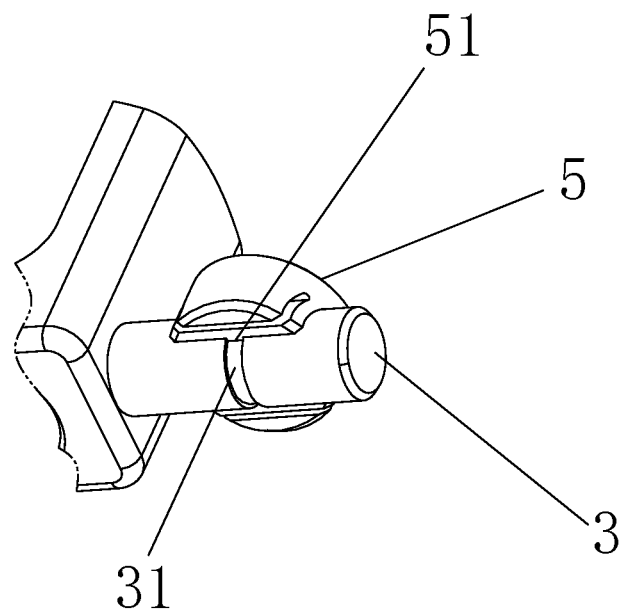
FIG. 7 is a schematic diagram of a structural principle of the pressing block and a connecting rod in the present disclosure.
Figure 8:
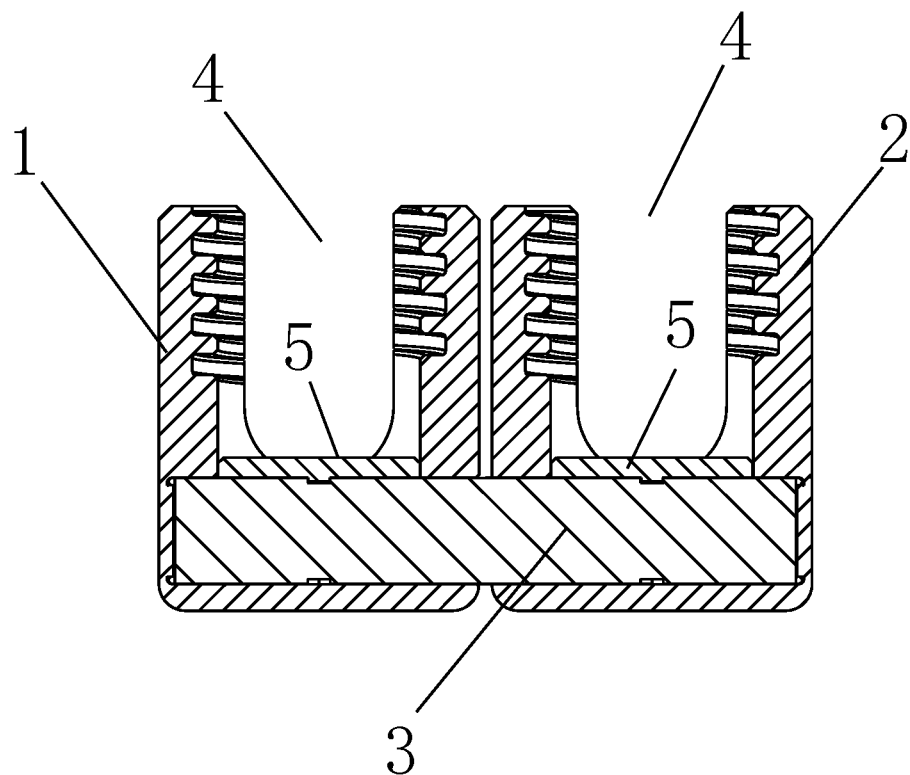
FIG. 8 is a schematic diagram of a second structure of the internal fixation apparatus according to the present disclosure.
Figure 9:
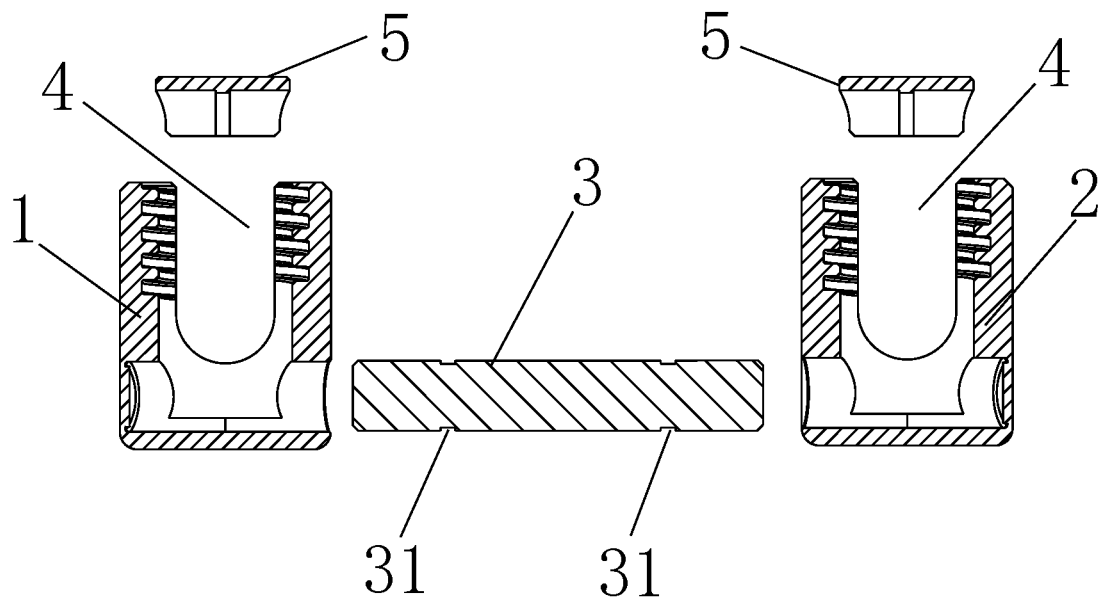
FIG. 9 is a decomposition diagram of FIG. 8.

With reference to FIGS. 7-9, a second structure of the adjustable double-slot internal spinal fixation apparatus according to the present disclosure is that one end of the connecting rod 3 is inserted in the first base 1 in a rotatable manner, and the other end of the connecting rod 3 is inserted in the second base 2 in a rotatable manner. That is, both the first base 1 and the second base 2 match the connecting rod 3 in a rotatable manner. The structure has the principle similar to that of the first structure. The U-shaped slot 4 on the second base 2 is connected with the long slot 21. U-shaped slots 4 of the first base 1 and the second base 2 each contains a pressing block 5 having identical structures. Limiting bumps 51 are included on bottom surfaces of the pressing blocks 5. The connecting rod 3 contains annular grooves 31 at both ends. One end of the connecting rod 3 is inserted to the bottom of the U-shaped slot 4 of the first base 1, and the other end of the connecting rod 3 is inserted to the bottom of the U-shaped slot 4 of the second base 2 through the long slot 21. The limit bumps 51 on the pressing blocks 5 fit with the annular grooves 31 on the connecting rod 3. That is, during use, two ends of the connecting rod 3 are inserted to the first base 1 and the second base 2 respectively, and the annular grooves 31 can be seen through the two U-shaped slots 4. When the two pressing blocks 5 are put into the U-shaped slots 4 respectively, the limit bumps 51 on the two pressing blocks 5 enter the respective annular grooves 31 for limiting, so that the connecting rod 3 can rotate with respect to the two bases freely, thereby achieving relative rotation between the first base 1 and the second base 2. In this embodiment, the positions of the two bases are also restricted by the limit bumps 51 and the annular grooves 31. Products of various models can also be produced according to varying distances between the two annular grooves 31. A swing fitting structure between the connecting rod 3 and the second base 2 in this embodiment is the same as that in Embodiment 1.

Figure 10:
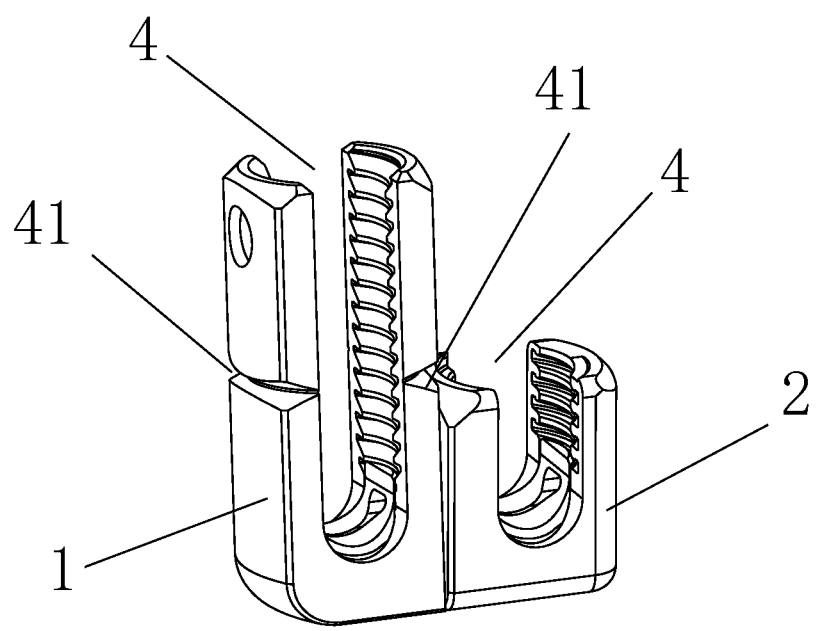
FIG. 10 is a schematic diagram of a first structure of the internal fixation apparatus according to the present disclosure having fracture notches.
Figure 11:
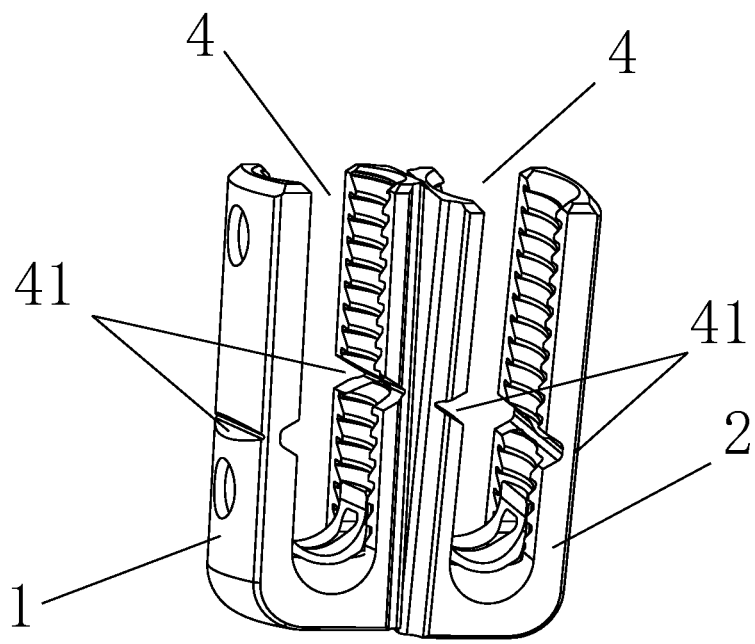
FIG. 11 is a schematic diagram of second structure of the internal fixation apparatus according to the present disclosure having fracture notches.

As shown in FIG. 10 and FIG. 11, two side walls of the U-shaped slot 4 of the first base 1 and/or two side walls of the U-shaped slot 4 of the second base 2 each contains a fracture notch 41. The fracture notch 41 can be fractured as required to meet surgical needs in different conditions. A structure is shown in FIG. 10. The first base 1 is higher than the second base 2, and the two side walls of the U-shaped slot 4 of the first base 1 each contains a fracture notch 41. When the fracture notch 41 is not fractured, the U-shaped slot 4 on the first base 1 can improve the rod disposing range in the U-shaped slot 4. When the fracture notches 41 are fractured, the first base 1 and the second base 2 have the same height. Another structure is shown in FIG. 11. The first base 1 and the second base 2 have the same height, and fracture notch 41 is included on each of the two side walls of the U-shaped slots 4 of the first base 1 and the second base 2. A structural principle and a using method are the same as those shown in FIG. 10

Figure 1:
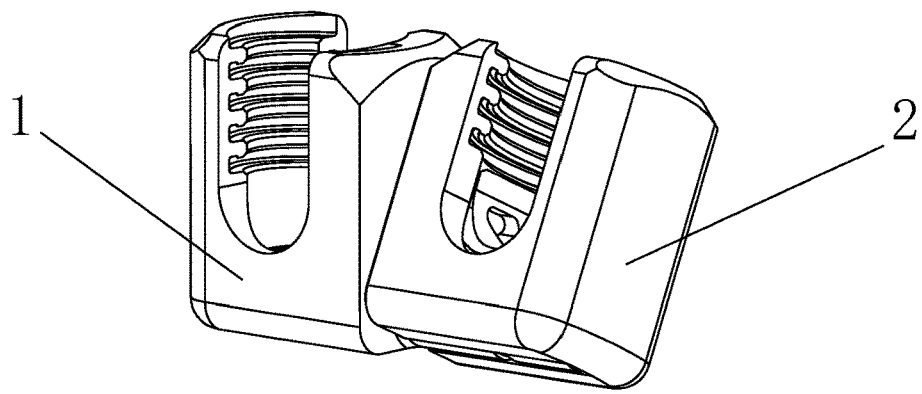
FIG. 1 is a schematic diagram of an internal fixation apparatus according to the present disclosure.
Figure 2:
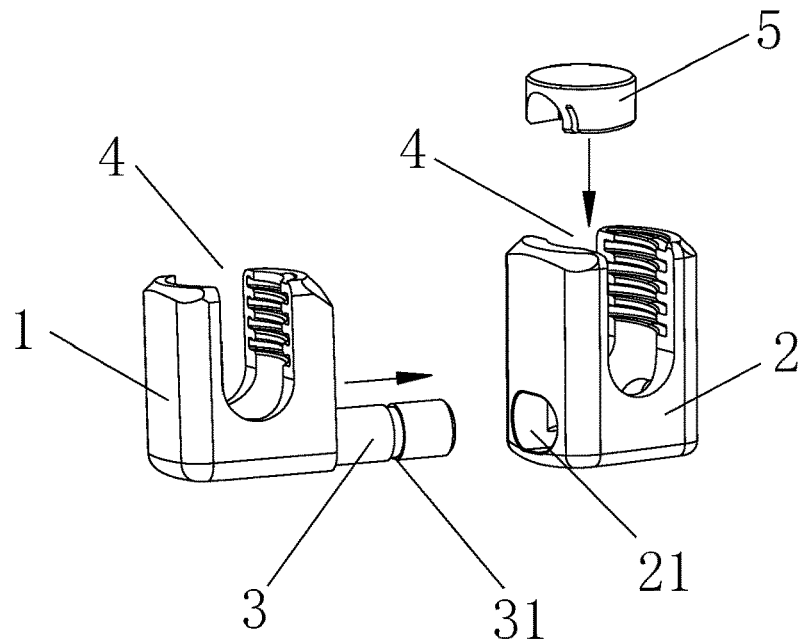
FIG. 2 is a decomposition diagram of a first structure of the internal fixation apparatus according to the present disclosure.
Figure 12:
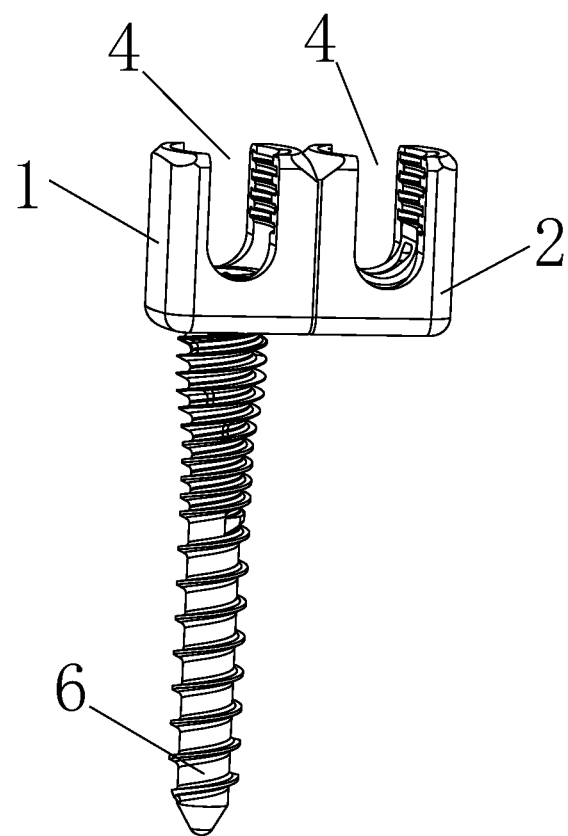
FIG. 12 is a schematic diagram of a first structure of a bone screw according to the present disclosure.
Figure 13:
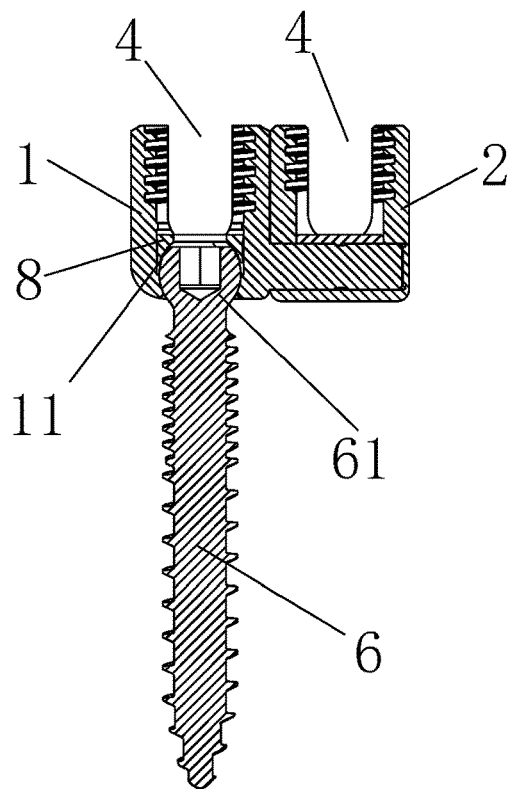
FIG. 13 is a cross-sectional view of FIG. 12.

With reference to FIG. 1, FIG. 12, and FIG. 13, the present disclosure further discloses a bone screw having the internal fixation apparatus. A screw rod 6 is included in the first base 1 and/or the second base 2. That is, the first base 1 and the second base 2 each contains a screw rod 6, or one of the first base 1 and the second base 2 contains a screw rod 6.

With reference to FIG. 12 and FIG. 13, a structure of this bone screw is as follows: the first base 1 contains a through hole 11 at the bottom of the U-shaped slot 4, and the through hole 11 is connected with a bottom surface of the first base 1. A ball socket is included in the through hole 11. A ball head 61 is included at one end of the screw rod 6. The screw rod 6 enters the through hole 11 through the U-shaped slot 4. When the ball head 61 and the ball socket properly fit each other, the screw rod 6 is installed in place. Then, a pressure head 8 is put into the U-shaped slot 4. The pressure head 8 is also of an inverted U-shaped structure and has two pressuring portions at a lower part. The pressing portions can press against the ball head 61 to limit the position of the ball head, that is, the first base 1 and the screw rod 6 are in universal fitting.

Figure 18:
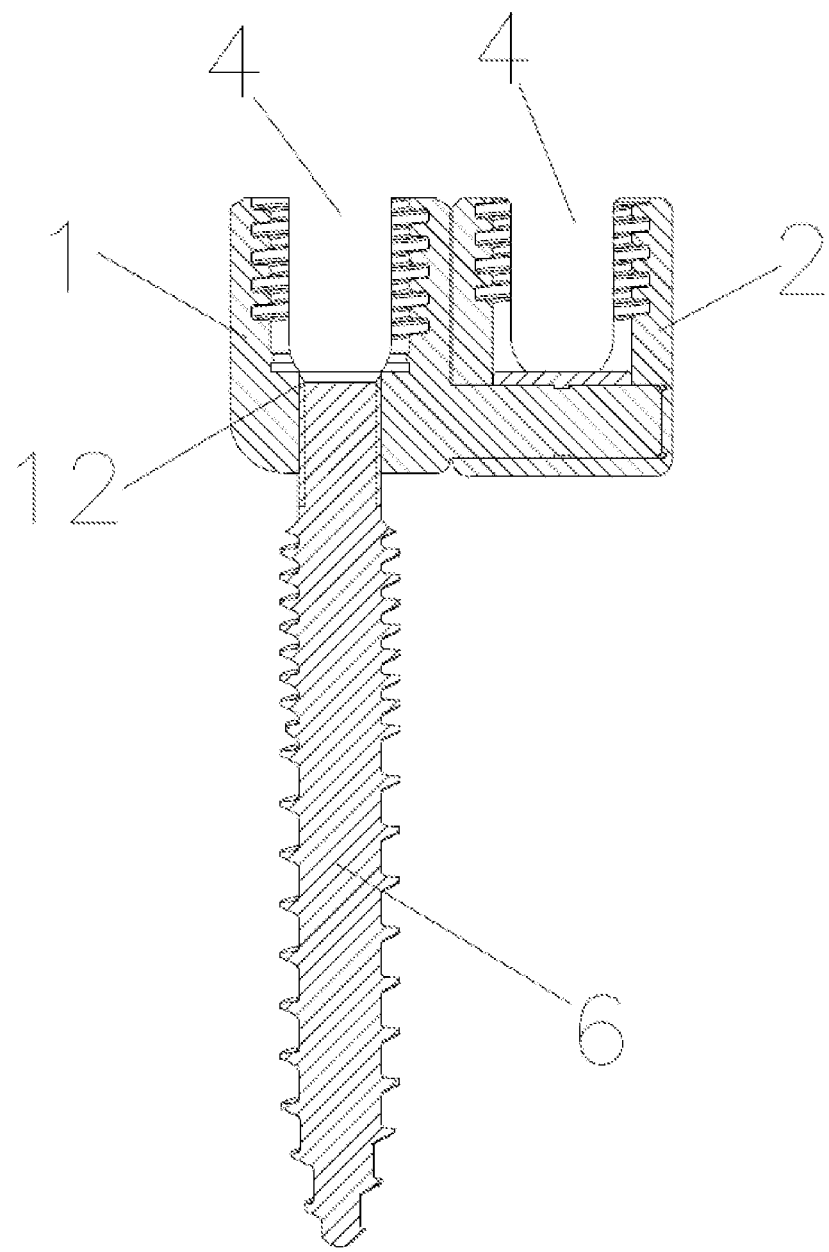
FIG. 18 is a schematic diagram of a fourth structure of the bone screw according to the present disclosure.

Referring to FIG. 18, another structure of this bone screw is as follows: the first base 1 and/or the second base 2 are/contains a threaded hole 12 at the bottom. The screw rod 6 and the threaded hole 12 match each other through threads, that is, they are fixed with respect to each other. In addition, the screw rod 6 can be welded on the first base 1 and/or the second base 2.

Figure 14:
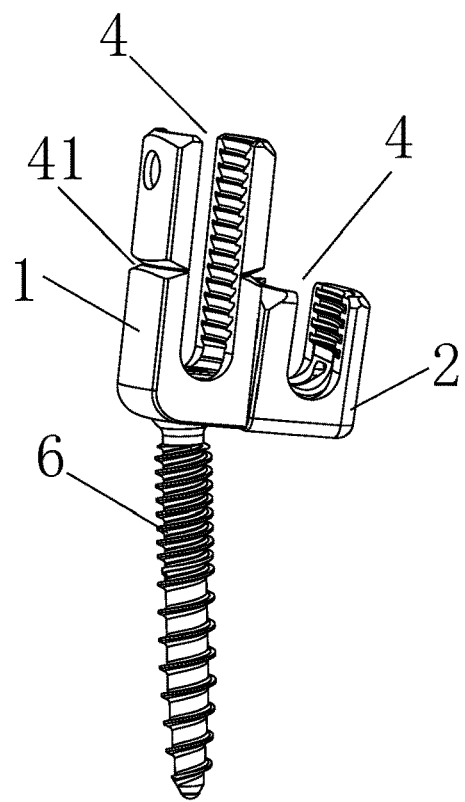
FIG. 14 is a schematic diagram of a second structure of the bone screw according to the present disclosure.
Figure 15:
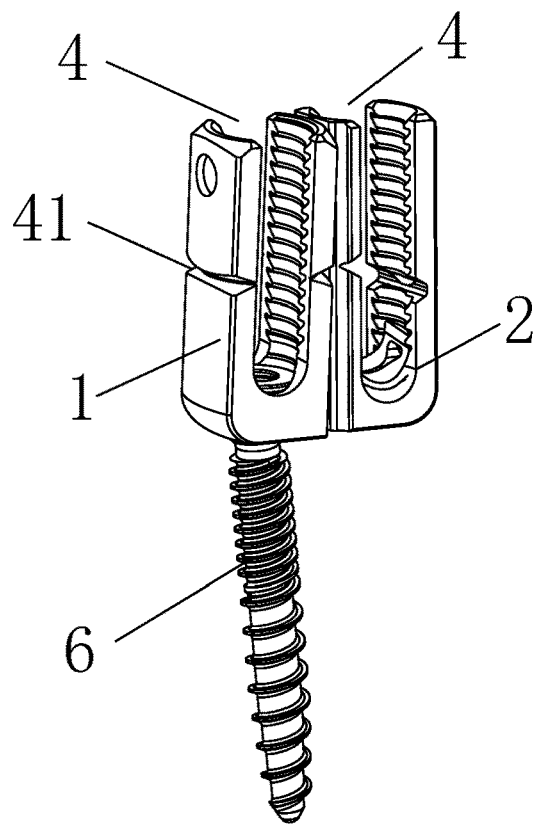
FIG. 15 is a schematic diagram of a third structure of the bone screw according to the present disclosure.

FIG. 14 and FIG. 15 are schematic structural diagrams of two types of bone screws having fracture notches 41.

Figure 16:
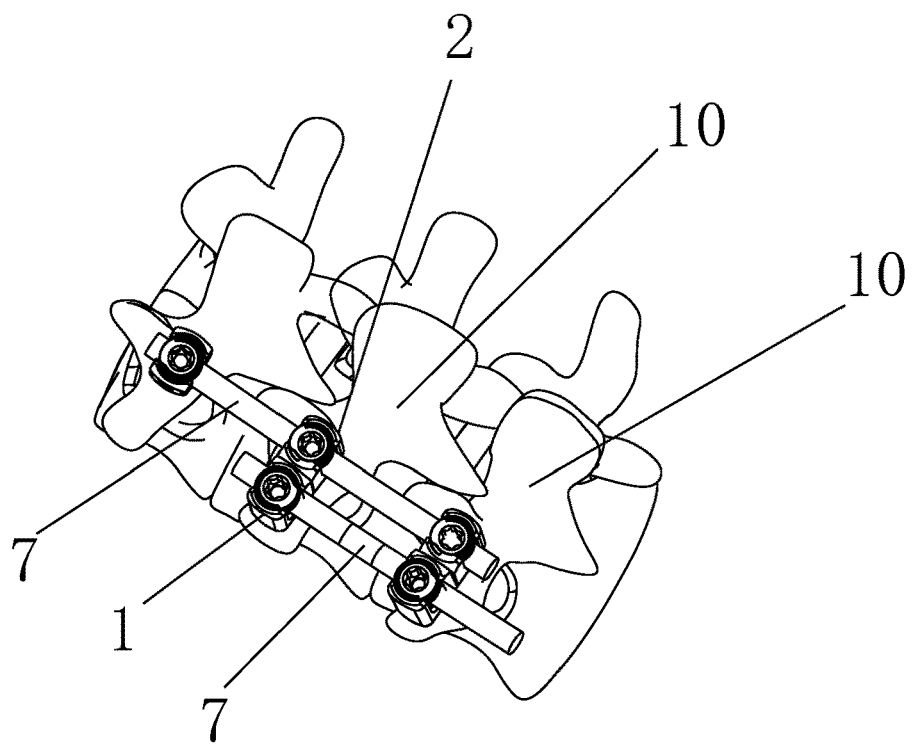
FIG. 16 is a schematic diagram of using the internal fixation apparatus according to the present disclosure.

FIG. 16 is a schematic diagram of use of an internal fixation apparatus according to the present disclosure. With reference to FIGS. 1-7, and FIG. 16, rods 7 are mounted on the first base 1 and the second base 2 respectively. The two rods 7 also fit with other bone screws. The first base 1 and the second base 2 are in a suspended state without being connected to vertebras 10. The first base 1 and the second base 2 rotate and swing relatively, so that the two rods 7 are guided without bending the rods 7, thereby achieving transition guiding.

Figure 17:
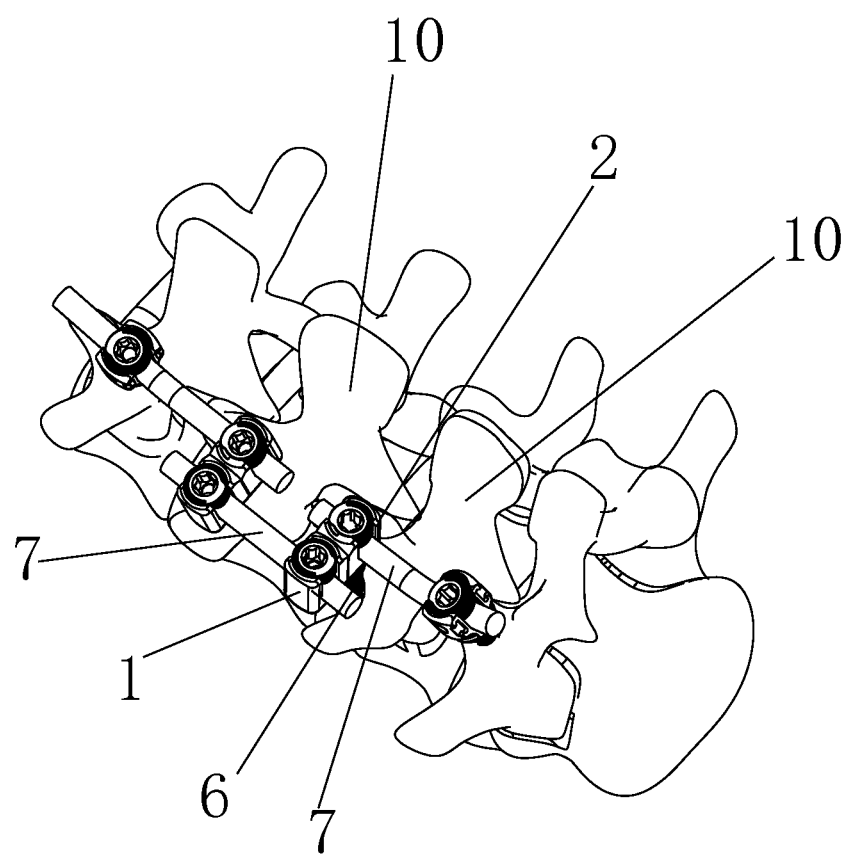
FIG. 17 is a schematic diagram of using the bone screw according to the present disclosure having the internal fixation apparatus.

In a spinal surgery, at positions where bone screws can be implanted, the bone screw according to the present disclosure having the internal fixation apparatus is used. As shown in FIG. 17, the second base 2 contains a screw rod 6. With reference to FIGS. 1-7, FIG. 12, and FIG. 17, the screw rod 6 on the second base 2 is screwed into the vertebra 10, to achieve overall positioning. Rods 7 are mounted on the first base 1 and the second base 2. The two rods 7 also fit with other bone screws. The bone screw according to the present disclosure achieves transition guiding for the two rods as well as positioning.

In conclusion, the adjustable double-slot internal spinal fixation apparatus and the bone screw according to the present disclosure can resolve the problems that rods are bent for too many times and operations are time-consuming and labor-consuming, thereby effectively improving the surgery efficiency. Therefore, the present disclosure effectively overcomes some practical problems in the prior art and hence achieves high utilization value and usage significance.

The foregoing embodiments are only to illustrate the principle and efficacy of the present disclosure exemplarily, and are not to limit the present disclosure. The present disclosure can be improved in many aspects without departing from the overall idea. Any person skilled in the art can make modifications or variations on the foregoing embodiments without departing from the spirit and scope of the present disclosure. Accordingly, all equivalent modifications or variations completed by those with ordinary skill in the art without departing from the spirit and technical thinking disclosed by the present disclosure should fall within the scope of the claims of the present disclosure.

What is claimed is:

1. An adjustable double-slot internal spinal fixation apparatus, comprising
    a first base (1), a second base (2), and a connecting rod (3), wherein
        the first base (1) and the second base (2) each contains a U-shaped slot (4) from top to bottom,
        an inner wall of each U-shaped slot (4) contains inner threads,
        the connecting rod (3) is disposed along a horizontal direction,
        the second base (2) contains a long slot (21) along the horizontal direction,
        the connecting rod (3) is capable of swinging in the long slot (21),
        the first base (1) and the second base (2) are capable of relatively rotating on the connecting rod (3),
        one end of the connecting rod (3) is fixedly connected to the first base (1), and the other end of the connecting rod (3) is inserted in the long slot (21) of the second base (2) in a rotatable manner,
        the U-shaped slot (4) on the second base (2) is connected with the long slot (21), a pressing block (5) is disposed in the U-shaped slot (4) of the second base (2), wherein the pressing block (5) has an inverted U-shaped structure adapted to a shape of the connecting rod (3), wherein
            the inverted U-shaped structure has two ends and includes an inner plate (52) and an outer plate (53) at each of the two ends, and a gap (54) is formed between the inner plate (52) and the outer plate (53), wherein a side of the inner plate (52) facing the connecting rod (3) has a shape adapted to an outer wall of the connecting rod (3),
            an annular groove (31) is formed around the connecting rod (3), the connecting rod (3) is inserted to the bottom of the U-shaped slot (4) through the long slot (21), and a limit bump (51) having an annular structure protrudes from the side of the inner plate (52) facing the connecting rod (3) and fits with the annular groove (31) to limit a position of the second base (2) on the connecting rod (3),
            the inner plate (52) is made of an elastic material, and is configured to be elastically deformed when the connecting rod (3) swings in the long slot (21), the connecting rod (3) is capable of rotating with respect to the pressing block (5), and
            the pressing block (5) is capable of rotating inside the U-shaped slot (4) in a horizontal plane while being static relative to the connecting rod (3) when the connecting rod (3) swings in the long slot (21).

2. The adjustable double-slot internal spinal fixation apparatus according to claim 1, wherein
    two side walls of the U-shaped slot (4) of the first base (1) and/or two side walls of the U-shaped slot (4) of the second base (2) each contains a fracture notch (41).

3. A bone screw, having the internal spinal fixation apparatus according to claim 1, wherein the first base (1) contains a screw rod (6).

4. The bone screw according to claim 3, wherein
    the first base (1) contains a ball socket,
    one end of the screw rod (6) contains a ball head, and
    the ball head fits with the ball socket.

5. The bone screw according to claim 3, wherein the first base (1) contains a threaded hole (12), and the screw rod (6) fits with the threaded hole (12) through threads.

* * * * *